United States Patent
Ali et al.

(10) Patent No.: US 12,180,235 B1
(45) Date of Patent: Dec. 31, 2024

(54) FABRICATION OF NOVEL NANO-SIZED [4{3,4-BIS-[(5-BROMO-2-HYDROXY-BENZYLIDENE)-AMINO]-PHENYL}-PHENYL-METHANONE] RU(III) COMPLEX FOR PHARMACEUTICAL APPLICATIONS

(71) Applicant: KING FAISAL UNIVERSITY, Al-Ahsa (SA)

(72) Inventors: Mai Mostafa Khalaf Ali, Al-Ahsa (SA); Hany Mohamed Abd El-Lateef Ahmed, Al-Ahsa (SA); Rafea Elamin Elgack Elgorashe, Al-Ahsa (SA); Mona M Abdel-Mawla, Sohag (EG); Rafat M. El-Khatib, Sohag (EG); Ibrahim Omar Barnawi, Madinah (SA); Amal H. Alsehli, Madinah (SA); Ahmed M. Abu-Dief, Madinah (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/439,677

(22) Filed: Feb. 12, 2024

(51) Int. Cl.
*C07F 15/00* (2006.01)
*A61K 9/51* (2006.01)
*A61P 31/04* (2006.01)
*A61P 31/10* (2006.01)
*A61P 35/00* (2006.01)
*A61P 39/06* (2006.01)

(52) U.S. Cl.
CPC ............ *C07F 15/0053* (2013.01); *A61K 9/51* (2013.01); *A61K 9/5192* (2013.01); *A61P 31/04* (2018.01); *A61P 31/10* (2018.01); *A61P 35/00* (2018.01); *A61P 39/06* (2018.01)

(58) Field of Classification Search
None
See application file for complete search history.

(56) References Cited

FOREIGN PATENT DOCUMENTS

| CN | 115850345 A | 3/2023 |
| CN | 116284146 A | 6/2023 |

OTHER PUBLICATIONS

Asadi et al., Journal of the Serbian Chemical Society (2011), 76(1), pp. 63-74.*
Abebe, Atakilt, and Tizazu Hailemariam. "Synthesis and assessment of antibacterial activities of ruthenium (III) mixed ligand complexes containing 1, 10-phenanthroline and guanide." Bioinorganic chemistry and applications 2016 (2016), article ID: 3607924, 9 pages.
Oter et al., "Photocharacterization of Novel Ruthenium Dyes and Their Utilities as Oxygen Sensing Materials in Presence of Perfluorochemicals", J. Fluoresc., 2007.
Al-Noaimi, Mousa, et al. "Ruthenium (II) quinoline-azoimine complex: Synthesis, crystalline structures spectroelectrochemistry and catalytic properties." Journal of Molecular Structure 1217 (2020): 128327.
Silva-Caldeira, Priscila Pereira, Antônio Carlos Almendagna de Oliveira Junior, and Elene Cristina Pereira-Maia. "Photocytotoxic Activity of Ruthenium (II) Complexes with Phenanthroline-Hydrazone Ligands." Molecules 26.7 (2021): 2084.
Lenis-Rojas, Oscar A., et al. "In Vitro and In Vivo Biological Activity of Ruthenium 1, 10-Phenanthroline-5, 6-dione Arene Complexes." International Journal of Molecular Sciences 23.21 (2022): 13594.
Kaulage, Mangesh H., et al. "Novel ruthenium azo-quinoline complexes with enhanced photonuclease activity in human cancer cells." European journal of medicinal chemistry 139 (2017): 1016-1029.
Nechmad et al., "Ruthenium benzylidene and benzylidyne complexes: Alkene metathesis catalysis", Reference Module in Chemistry, Molecular Sciences and Chemical Engineering, Jan. 2022. (Abstract).

* cited by examiner

*Primary Examiner* — Brian J Davis
(74) *Attorney, Agent, or Firm* — Nath, Goldberg & Meyer; Joshua B. Goldberg

(57) ABSTRACT

A nano-sized [4{3,4-bis-[(5-bromo-2-hydroxy-benzylidene)-amino]-phenyl}-phenyl-methanone] Ru(III) complex, its synthesis, and its use as an anticancer, antioxidant, and antimicrobial agent.

18 Claims, 3 Drawing Sheets

FABRICATION OF NOVEL NANO-SIZED [4{3,4-BIS-[(5-BROMO-2-HYDROXY-BENZYL-IDENE)-AMINO]-PHENYL }-PHENYL-METHANONE] RU(III) COMPLEX FOR PHARMACEUTICAL APPLICATIONS

BACKGROUND

1. Field

The present disclosure relates to a nano-sized [4{3,4-bis-[(5-bromo-2-hydroxy-benzylidene)-amino]-phenyl}-phenyl-methanone] Ru(III), its synthesis, and its use as an antitumor, antioxidant, and/or antimicrobial agent.

2. Description of the Related Art

There remains an ongoing need for new therapeutically active agents for treating a variety of diseases, disorders, and conditions including, but not limited to, various forms of cancer, various microbial infections, and the like.

Over recent decades, supramolecular chemistry has become a matter of interest. The design and development of new biomaterials and their molecular frameworks have increased rapidly, addressing the coordination chemistry of biologically active chelates. Schiff base compounds have received a lot of attention from researchers. Schiff bases are useful in many different areas such as polymer stabilizers, catalysts, and intermediates in organic synthesis, dyes, and pigments. Furthermore, Schiff bases are an essential class of ligands in coordination chemistry. Schiff bases have also been demonstrated to have antibacterial, antifungal, antimalarial, antiviral, anti-inflammatory, and antipyretic effects, among other biological actions.

On the other hand, cancer is killing millions of people worldwide, and the design of small molecules (metal-based drugs) that bind and react at specific sequences with CT-DNA are especially important in the development of new therapeutic reagents.

Thus, new molecules having desired therapeutic activities and solving the aforementioned problems are desired.

SUMMARY

The present subject matter relates to a nano-sized [4{3, 4-bis-[(5-bromo-2-hydroxy-benzylidene)-amino]-phenyl}-phenyl-methanone] Ru(III) complex. The creation of a novel compound with unique physical, chemical, and biological properties results from the synthesis of nano-sized complexes. The 1st row of transition metal chelates has numerous uses in various domains. Due to the advantages of these components, 4{3,4-bis-[(5-bromo-2-hydroxy-benzylidene)-amino]-phenyl}-phenyl-methanone was synthesized as a ligand.

The prepared nano-sized 4{3,4-bis-[(5-bromo-2-hydroxy-benzylidene)-amino]-phenyl}-phenyl-methanone-Ru(III) complex can have superior pharmaceutical applications compared to standard drugs The Schiff base H2L ligand may be used to synthesize novel nano complex with $RuCl_3 \cdot 3H_2O$. The prepared ligand and nano Ru(III) complex was deduced by different spectroscopic techniques. The nano-sized Ru(III) complex was synthesized in an environmentally friendly. The structure, morphologies and particle size of the nano-sized complexes were determined using FT-IR, TEM, and PXRD. The results displayed that the nano-domain chelate is on the Sub-nano scale. Experimental data were supported by DFT calculations. The findings revealed that the nano-metal complexes investigated are more stable than the studied free ligand.

In an embodiment, the present subject matter relates to a nano-sized [4{3,4-bis-[(5-bromo-2-hydroxy-benzylidene)-amino]-phenyl}-phenyl-methanone] Ru(III) complex having the formula I:

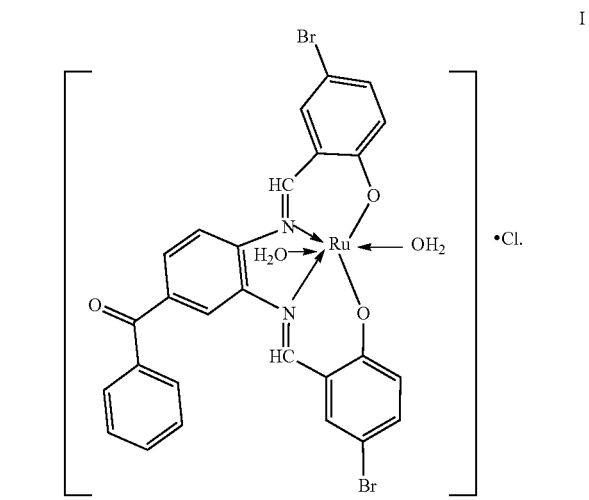

In another embodiment, the present subject matter relates to a therapeutically effective amount of the nano-sized [4{3,4-bis-[(5-bromo-2-hydroxy-benzylidene)-amino]-phenyl}-phenyl-methanone] Ru(III) complex as described herein and a pharmaceutically acceptable carrier.

In a further embodiment, the present subject matter relates to a method of treating cancer in a patient comprising administering to a patient in need thereof a therapeutically effective amount of the nano-sized [4{3,4-bis-[(5-bromo-2-hydroxy-benzylidene)-amino]-phenyl}-phenyl-methanone] Ru(III) complex.

In an embodiment, the present subject matter relates to a method of treating a microbial infection in a patient comprising administering to a patient in need thereof a therapeutically effective amount of the nano-sized [4{3,4-bis-[(5-bromo-2-hydroxy-benzylidene)-amino]-phenyl}-phenyl-methanone] Ru(III) complex.

In another embodiment, the present subject matter relates to a method of inhibiting free radicals in a patient comprising administering to a patient in need thereof a therapeutically effective amount of the nano-sized [4{3,4-bis-[(5-bromo-2-hydroxy-benzylidene)-amino]-phenyl}-phenyl-methanone] Ru(III) complex.

In one more embodiment, the present subject matter relates to a method of making the nano-sized [4{3,4-bis-[(5-bromo-2-hydroxy-benzylidene)-amino]-phenyl}-phenyl-methanone] Ru(III) complex, the method comprising: adding $RuCl_3$ in ethanol to a 4{3,4-Bis-[(5-bromo-2-hydroxy-benzylidene)-amino]-phenyl}-phenyl-methanone azomethine ligand in ethanol to obtain a reaction mixture; sonicating the reaction mixture a first time; adding a secondary ligand phenanthroline to the reaction mixture under sonication a second time; and obtaining the nano-sized [4{3,4-bis-[(5-bromo-2-hydroxy-benzylidene)-amino]-phenyl}-phenyl-methanone] Ru(III) complex.

These and other features of the present subject matter will become readily apparent upon further review of the following specification.

DETAILED DESCRIPTION OF THE PREFERRED EMBODIMENTS

Figure 1:
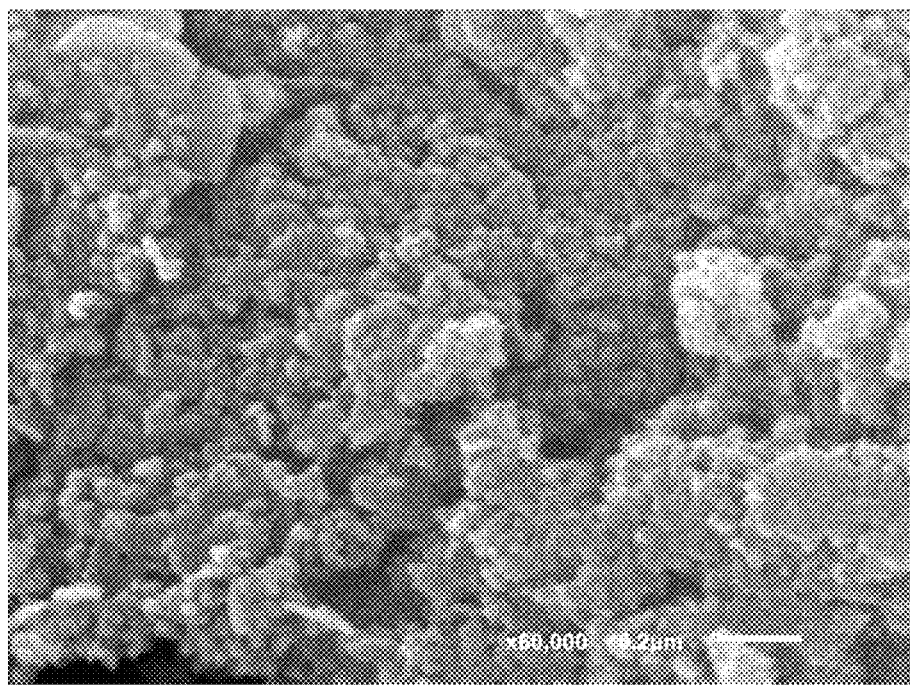
FIG. 1 shows a SEM of the prepared nano-sized 4{3,4-Bis-[(5-bromo-2-hydroxy-benzylidene)-amino]-phenyl}-phenyl-methanone-Ru(III) complex.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer, antimicrobial infections, and free radicals.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a nano-sized [4{3,4-bis-[(5-bromo-2-hydroxy-benzylidene)-amino]-phenyl}-phenyl-methanone] Ru(III) complex. The creation of novel compounds with unique physical, chemical, and biological properties results from the synthesis of nano-sized complexes. The first row of transition metal chelates has numerous uses in various domains. Due to the advantages of these components, 4{3,4-bis-[(5-bromo-2-hydroxy-benzylidene)-amino]-phenyl}-phenyl-methanone was synthesized as a ligand.

The Schiff base H2L ligand may be used to synthesize a novel nano complex with $RuCl_3 \cdot 3H_2O$. The prepared ligand and nano Ru(III) complex was deduced by different spectroscopic techniques. The nano-sized Ru(III) complex was synthesized in an environmentally friendly. The structure, morphologies and particle size of the nano-sized complexes were determined using FT-IR, TEM, and PXRD. The results displayed that the nano-domain chelate is on the Sub-nano scale. Experimental data were supported by DFT calculations. The findings revealed that the nano-metal complexes investigated are more stable than the studied free ligand.

In an embodiment, the present subject matter relates to a nano-sized [4{3,4-bis-[(5-bromo-2-hydroxy-benzylidene)-amino]-phenyl}-phenyl-methanone] Ru(III) complex having the formula I:

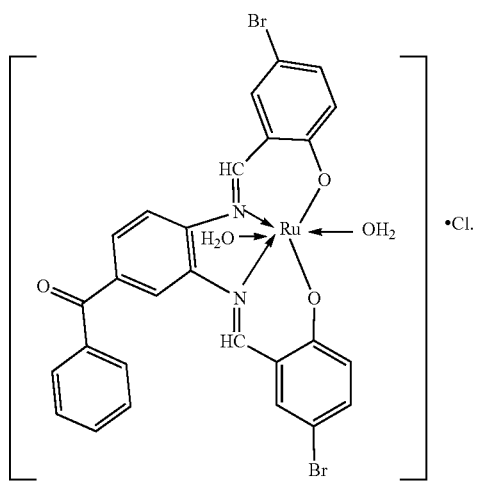

In certain embodiments, the nano-sized [4{3,4-bis-[(5-bromo-2-hydroxy-benzylidene)-amino]-phenyl}-phenyl-methanone] Ru(III) complex may have a spherical shape. In further embodiments, the 2 nano-sized [4{3,4-bis-[(5-bromo-2-hydroxy-benzylidene)-amino]-phenyl}-phenyl-methanone] Ru(III) complex may have a size of about 20 nm.

In another embodiment, the present subject matter relates to a pharmaceutically acceptable composition comprising a therapeutically effective amount of the nano-sized [4{3,4-bis-[(5-bromo-2-hydroxy-benzylidene)-amino]-phenyl}-phenyl-methanone] Ru(III) complex and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for cancer, a microbial infection, or use as an antioxidant. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of cancer, a microbial infection, and/or an oxidative condition, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction.

For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In a further embodiment, the present subject matter relates to a method of treating cancer in a patient comprising administering to a patient in need thereof a therapeutically effective amount of the nano-sized [4{3,4-bis-[(5-bromo-2-hydroxy-benzylidene)-amino]-phenyl}-phenyl-methanone] Ru(III) complex.

In certain embodiments in this regard, the cancer can be colon cancer.

In another embodiment, the present subject matter relates to a method of treating a microbial infection in a patient comprising administering to a patient in need thereof a therapeutically effective amount nano-sized [4{3,4-bis-[(5-bromo-2-hydroxy-benzylidene)-amino]-phenyl}-phenyl-methanone] Ru(III) complex. In certain embodiments, the microbial infection may be caused by a gram negative bacteria such as, by way of non-limiting example, *Pseudomonas aeruginosa*. In other embodiments, the microbial infection may be caused by a fungus, such as, by way of non-limiting example, *Aspergillus Flavus*.

In an embodiment, the present subject matter relates to a method of inhibiting free radicals in a patient comprising administering to a patient in need thereof a therapeutically effective amount of a nano-sized [4{3,4-bis-[(5-bromo-2-hydroxy-benzylidene)-amino]-phenyl}-phenyl-methanone] Ru(III) complex. In a further embodiment, the present subject matter relates to a method of promoting antioxidant activity in a subject, the method comprising administering to a subject in need thereof the pharmaceutical composition including a therapeutically effective amount of a nano-sized [4{3,4-bis-[(5-bromo-2-hydroxy-benzylidene)-amino]-phenyl}-phenyl-methanone] Ru(III) complex In one more embodiment, the present subject matter relates to a method of making a nano-sized [4{3,4-bis-[(5-bromo-2-hydroxy-benzylidene)-amino]-phenyl}-phenyl-methanone] Ru(III) complex, the method comprising: adding $RuCl_3$ in ethanol to a 4{3,4-Bis-[(5-bromo-2-hydroxy-benzylidene)-amino]-phenyl}-phenyl-methanone azomethine ligand in ethanol to obtain a reaction mixture; sonicating the reaction mixture a first time; adding a secondary ligand phenanthroline to the reaction mixture under sonication a second time; and obtaining the nano-sized

[4{3,4-bis-[(5-bromo-2-hydroxy-benzylidene)-amino]-phenyl}-phenyl-methanone] Ru(III) complex.

Figure 3:
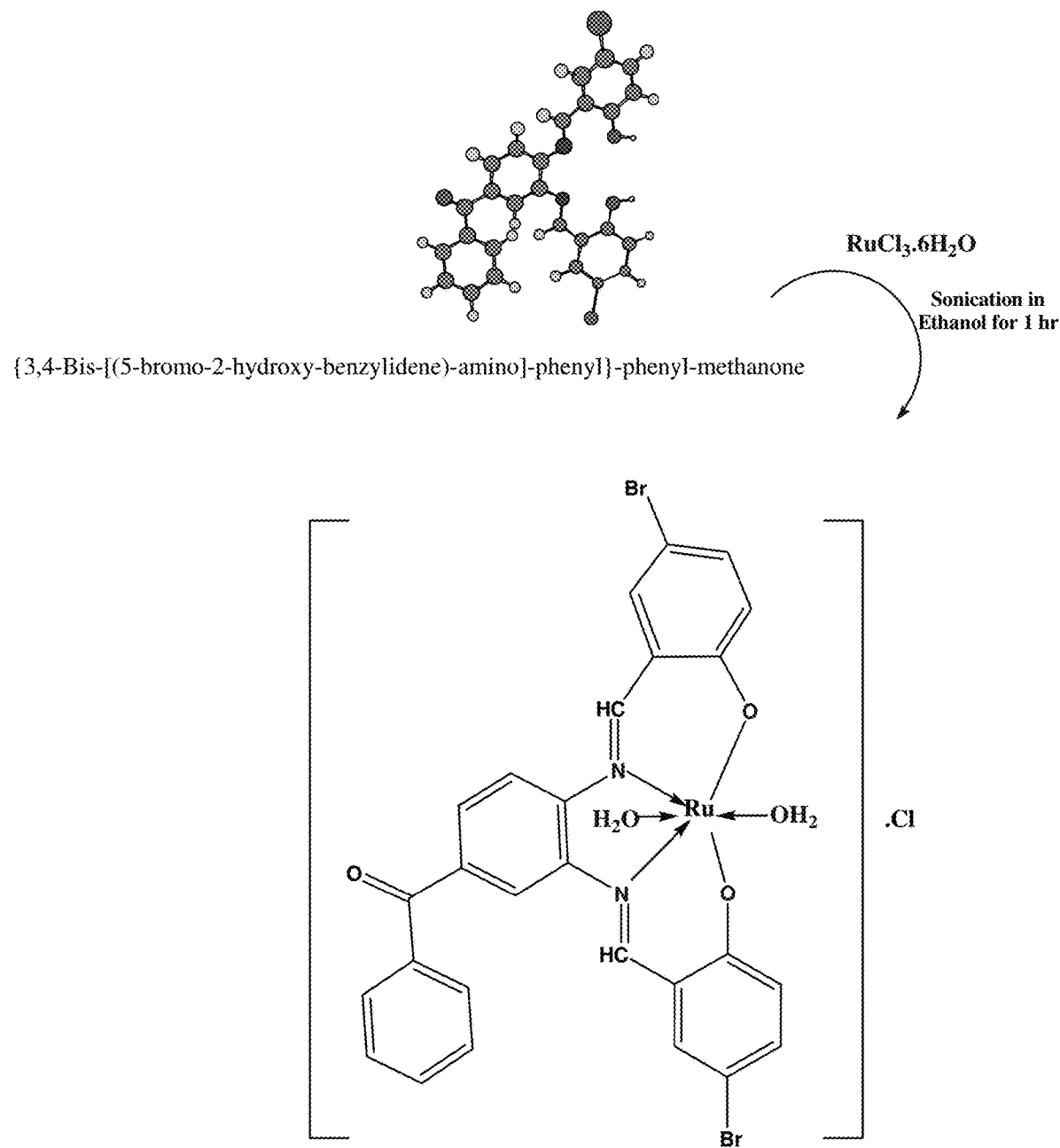
FIG. 3 shows reaction Scheme I illustrating a method of making a nano-sized [4{3,4-bis-[(5-bromo-2-hydroxy-benzylidene)-amino]-phenyl}-phenyl-methanone] Ru(III) complex.

The present production methods can be further seen by referring to the reaction Scheme 1 as shown in FIG. 3.

In an embodiment of the present production methods, the RuCl$_3$ in ethanol may be added stepwise.

In another embodiment of the present production methods, sonicating the reaction mixture a first time may last for about 30 minutes.

In a further embodiment of the present production methods, sonicating the reaction mixture a second time may last for about 30 minutes.

In an embodiment of the present production methods, wherein the RuCl$_3$ and the 4{3,4-Bis-[(5-bromo-2-hydroxy-benzylidene)-amino]-phenyl}-phenyl-methanone azomethine ligand may be added in an about 2:1 molar ratio. Similarly, the RuCl$_3$, the 4{3,4-Bis-[(5-bromo-2-hydroxy-benzylidene)-amino]-phenyl}-phenyl-methanone azomethine ligand, and the secondary ligand phenanthroline can be added in an about 2:1:1 molar ratio.

In an additional embodiment of the present production methods, the nano-sized [4{3,4-bis-[(5-bromo-2-hydroxy-benzylidene)-amino]-phenyl}-phenyl-methanone] Ru(III) complex can be obtained as a dark brown crystalline powder.

The following examples relate to various methods of manufacturing the specific compounds and application of the same, as described herein. All compound numbers expressed herein are with reference to the synthetic pathway figures shown above.

EXAMPLES

Example 1

Preparation of the Nano-Sized [4{3,4-bis-[(5-bromo-2-hydroxy-benzylidene)-amino]-phenyl}-phenyl-methanone] Ru(III) Complex Hexahydropyridine (200 mmole) was added to a three necked flask (150 ml) with a magnetic stirrer. An (20 mmol) equimolar quantity of H$_2$SO$_4$ (concentrated) was added sluggishly into the flask at an ice path. The mixture of the reaction was then stirred at 79° C. for 12 hrs, washed with ethoxyethane many times to isolate non-ionic deposits and dried in vacuum on a rotary evaporator to produce piperidinium hydrogen sulfate as a sticky liquefied compound.

The elemental analysis for the prepared nano complex was analyzed at room temperature by C, H and N elemental percentage analyses using the GMBH EI V2.3 model and the results as follows:

Chemical formula: 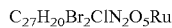 $C_{27}H_{20}Br_2ClN_2O_5Ru$

The experimental data of CHN were in a good agreement with calculated percent as follows: Found (Calculated) C, 44.25 (44.20); H, 2.62 (2.65); N, 3.71 (3.68); Ru, 13.35 (13.28)

Figure 2:
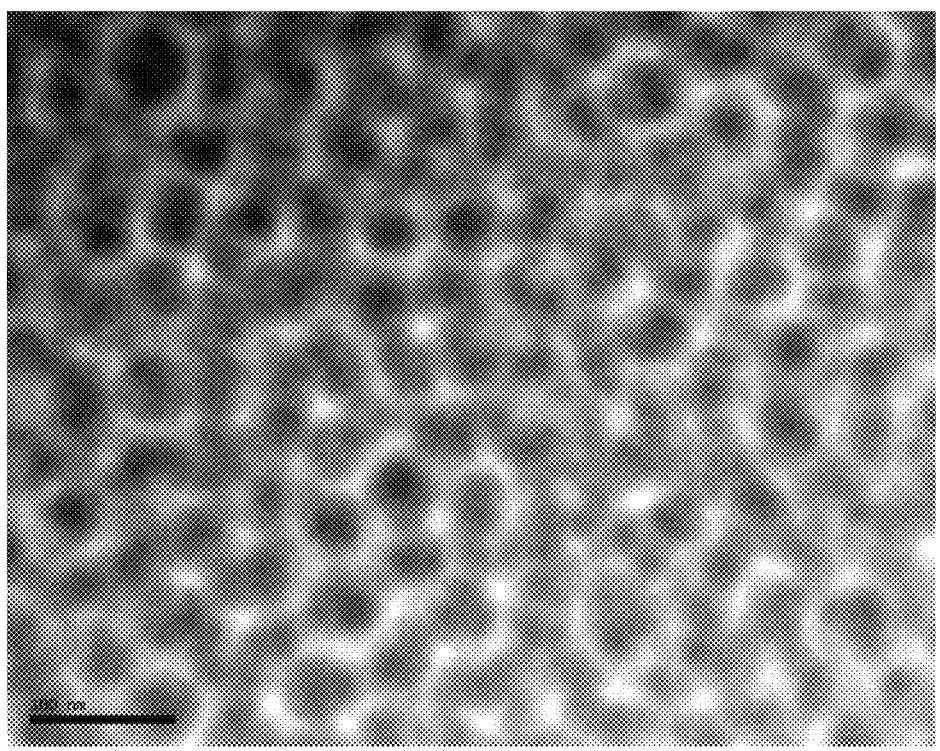
FIG. 2 shows a TEM of the prepared nano-sized 4{3,4-Bis-[(5-bromo-2-hydroxy-benzylidene)-amino]-phenyl}-phenyl-methanone-Ru(III) complex.

Characterization of the prepared nano-complex using SEM and TEM analysis as shown in FIGS. 1 and 2, respectively. The prepared complex is nanoparticle with spherical in shape. According to TEM, the average size of the prepared nano complex is 20 nm. This affects directly on super medicinal application of the prepared complex.

Example 2

Anti-Microbial Activity

Antibacterial Screening of the Prepared Nano-Complex

The susceptibilities of such growth rate of microorganisms were measured in vitro by agar well diffusion method. The tested nano complex was dissolved in dimethylsulfoxide at different concentrations (10 and 20 mg/ml). 1 cm$^3$ of a 24 h broth culture containing 106 CFU/cm$^3$ was placed in sterile Petri-dishes. Molten nutrient agar (15 cm$^3$) maintained at 45° C. was then poured into the Petri-dishes and allowed to solidify. Then holes of 6 mm diameter were formed in the agar using a sterile cork borer and these holes were completely filled with the test solutions. The plates were incubated for 24 hours at 37° C. After the incubation period, the zone of inhibition of each well was determined by measuring the zones of growth inhibition (mm) against the test microorganisms with zone reader (Hi Antibiotic zone scale). In order to clarify the effect of solvent (DMSO) on the biological screening, DMSO alone was used as control, and it showed no activity against microbial strains. The measurements were made in triplicate for each compound and their average values are reported.

Antifungal Screening of the Prepared Nano-Complex

Antifungal activities of the prepared nano-complex were studied against three fungal cultures using well diffusion method. The tested fungi were inoculated in Sabouraud dextrose broth medium (Hi-Media Mumbai) and incubated at 35° C. for 72 h and subsequently a suspension of about 1.60×10$^4$-6.00×10$^4$ c.f.u/ml was introduced agar plates and a sterile glass spreader was used for even distribution of the inoculum. The discs measuring 6 mm in diameter were prepared from Whatman No. 1 filter paper and sterilized by dry heat at 140° C. for 1 h. The sterile discs previously soaked in known concentration of the tested compounds were placed in Sabouraud dextrose Agar (SDA) plates. The plates were inverted and incubated at 35° C. for 7 days. The susceptibility was assessed on the basis of diameter of inhibition against *albicans* and non-*albicans* strain of fungi.

Minimum Inhibitory Concentrations (MICs) of the Prepared Nano-Complex

Minimum inhibitory concentrations (MICs) are defined as the lowest concentration of an antimicrobial that will inhibit the visible growth of a microorganism after overnight incubation. MICs are used by diagnostic laboratories mainly to confirm resistance of microorganism to antimicrobial agents and also to monitor the activity of new antimicrobial agents. MIC was determined in vitro in liquid medium by serial broth dilution method. The MIC values keep up a correspondence to the most minuscule concentrations that did not allow for the recognition of any visible growth.

Results of Anti-Microbial Activity

The prepared nano complex shows potent antibacterial activity against *Pseudomonas aeruginosa* bacteria with inhibition zone 42 mm and MIC 1.5 µg/ml compared with standard drug Ofloxacin (38 mm and MIC 2.25 µg/ml). Moreover, it shows anti-fungal activity against *Aspergillus Flavus* with inhibition zone of 30 mm and MIC 2.00 µg/ml compared with standard drug Flucazanol (27 mm and MIC 2.50 µg/mL).

Example 3

Anti-Cancer Activity

Protocol for Anticancer Activity of the Prepared Nano-Complex

The anticancer activity was made at the National Cancer Institute, Cancer Biology Department, Pharmacology Department, Cairo University. The absorbance or optical density (O.D.) of each well was measured spectrophotometrically at 564 (nm) with an "ELIZA" micro plate reader (Meter tech. Σ 960, "USA"). Evaluation of the cytotoxic activity of the prepared nano-complex was carried out against Colon cancer cells line. The evaluation process was carried out in vitro using the Sulfo-Rhodamine-B-stain (SRB). Cells were placed in 96-multiwell plate ($10^4$ cells/well) for 24 hrs before processing with the complexes to allow attachment of cell to the wall of the plate. Various concentrations of the compounds under test in DMSO (0, 1, 2.5, 5 and 10 UM) were added to the cell monolayer. Monolayer cells were incubated with the complexes for 48 hrs at 37° C. and in atmosphere of 5% $CO_2$. After 48 hrs, cells were fixed, rinsed, and stained with Sulfo-Rhodamine-B-stain. Excess stain was washed with acetic acid and attached stain was treated with Tris EDTA buffer. Color intensity was measured in an ELISA reader. $IC_{50}$ was evaluated and potency was calculated with regard to percentage of change of (vistabline standard). The relation between surviving fraction and compound concentration is plotted to get the survival curve of each tumor cell line after the specified compound. The experiment was carried out once and each concentration repeated 3 times.

The inhibitory concentration percent (IC %) was estimated according to the equation: Inhibition concentration (IC) %=(Control O.D.–Ligand O.D.)×100/Control O.D Results for Anti-Cancer Activity The prepared nano complex shows super anticancer activity with an $IC_{50}$ of 2.00 µg/µl against a colon cancer cell line compared with the vinblastine standard drug ($IC_{50}$=5.7 µg/µl).

Example 4

Anti-Oxidant Activity

Protocol for Antioxidant Assay (DPPH Free Radical Scavenging Activity)

In vitro antioxidant activity of the nano-complex herein was evaluated using scavenging the stable DPPH radical modified method. The model of scavenging the stable DPPH radical is a method that is widely used to evaluate antioxidant activities in a relatively short time compared with other methods. DPPH' radical scavenging test relies on the absorbance change of the radical when deactivated by antioxidants, which easily observable with naked eye as color changes from purple to yellow. Stock solutions of the investigated compounds were dissolved in methanol-DMSO (4:1) was diluted to final concentration of 10, 25, 50, 100 and 150 M. Methanolic DPPH (2,2-diphenyl-1-picrylhydrazyl) solution (1 mL, 0.3 mmol) was added to 3.0 mL of the synthesized compounds as well as standard compound (Ascorbic acid). The tube was protected from light by covering with aluminum foil and the absorbance was measured at 517 nm after 30 min. using methanol as a blank. All the tests were made in triplicates. Vitamin C was used as standard or positive control, parallel to the test compound and in the absence of the test compound/standard used as the negative control. The reduction in the absorbance of DPPH was calculated relative to the measured absorbance of the control. Lower absorbance values of reaction mixture indicated higher free-radical-scavenging activity. The percentage of DPPH radical scavenging activity was calculated using the below equation:

$$\% \ DPPH \ \text{scavenging activity} = \frac{A_C - A_S}{A_C}$$

where $A_C$ is the absorbance of the L-ascorbic acid (Standard) and $A_S$ is the absorbance of different compounds.

The methanolic DPPH solution (1 mL, 0.3 mM) was used as control. The effective concentration of sample required to scavenge DPPH radical by 50% ($IC_{50}$ value) was obtained by linear regression analysis of dose-response curve plotting between % inhibition and concentrations.

Results of Anti-Oxidant Activity

The prepared nano complex shows super anti-oxidant activity with an $IC_{50}$ of 6.00 µg/µl against a colon cancer cell line compared with the l-ascorbic acid standard antioxidant (IC50=49 µg/µl).

It is to be understood that the nano-sized [4{3,4-bis-[(5-bromo-2-hydroxy-benzylidene)-amino]-phenyl}-phenyl-methanone] Ru(III) complex, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A nano-sized [4{3,4-bis-[(5-bromo-2-hydroxy-benzylidene)-amino]-phenyl}-phenyl-methanone] Ru(III) complex having the formula I:

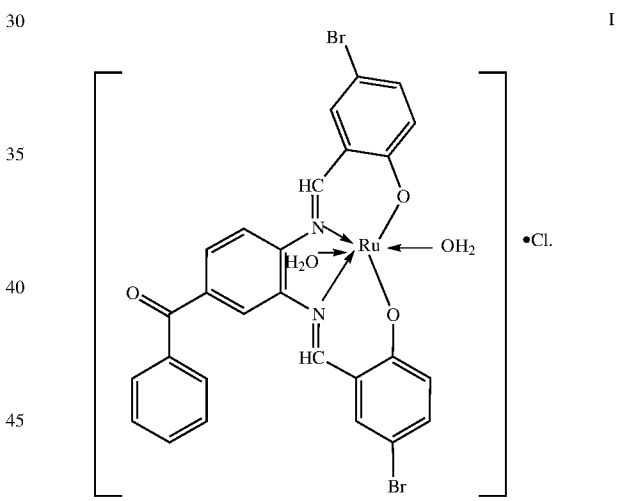

2. The nano-sized [4{3,4-bis-[(5-bromo-2-hydroxy-benzylidene)-amino]-phenyl}-phenyl-methanone] Ru(III) complex of claim 1, wherein the complex has a spherical shape.

3. The nano-sized [4{3,4-bis-[(5-bromo-2-hydroxy-benzylidene)-amino]-phenyl}-phenyl-methanone] Ru(III) complex of claim 1, wherein the complex has a size of about 20 nm.

4. A pharmaceutically acceptable composition comprising the nano-sized [4{3,4-bis-[(5-bromo-2-hydroxy-benzylidene)-amino]-phenyl}-phenyl-methanone] Ru(III) complex of claim 1 and a pharmaceutically acceptable carrier.

5. A method of treating cancer in a patient comprising administering to a patient in need thereof a therapeutically effective amount of the nano-sized [4{3,4-bis-[(5-bromo-2-hydroxy-benzylidene)-amino]-phenyl}-phenyl-methanone] Ru(III) complex of claim 1.

6. The method of treating cancer of claim 5, wherein the cancer is colon cancer.

7. A method of treating a microbial infection in a patient comprising administering to a patient in need thereof a therapeutically effective amount of the nano-sized [4{3,4-bis-[(5-bromo-2-hydroxy-benzylidene)-amino]-phenyl}-phenyl-methanone] Ru(III) complex of claim 1.

8. The method of treating the microbial infection of claim 7, wherein the microbial infection is caused by a gram negative bacteria *Pseudomonas aeruginosa*.

9. The method of treating the microbial infection of claim 7, wherein the microbial infection is caused by a fungus *Aspergillus Flavus*.

10. A method of inhibiting free radicals in a patient comprising administering to a patient in need thereof a therapeutically effective amount of the nano-sized [4{3,4-bis-[(5-bromo-2-hydroxy-benzylidene)-amino]-phenyl}-phenyl-methanone] Ru(III) complex of claim 1.

11. A method of promoting an antioxidant activity in a subject, the method comprising administering to a subject in need thereof the pharmaceutical composition of claim 4.

12. A method of making the nano-sized [4{3,4-bis-[(5-bromo-2-hydroxy-benzylidene)-amino]-phenyl}-phenyl-methanone] Ru(III) complex of claim 1, the method comprising:

adding $RuCl_3$ in ethanol to a 4{3,4-Bis-[(5-bromo-2-hydroxy-benzylidene)-amino]-phenyl}-phenyl-methanone azomethine ligand in ethanol to obtain a reaction mixture;

sonicating the reaction mixture a first time;

adding a secondary ligand phenanthroline to the reaction mixture under sonication a second time; and obtaining the nano-sized [4{3,4-bis-[(5-bromo-2-hydroxy-benzylidene)-amino]-phenyl}-phenyl-methanone] Ru(III) complex.

13. The method of making nano-sized [4{3,4-bis-[(5-bromo-2-hydroxy-benzylidene)-amino]-phenyl}-phenyl-methanone] Ru(III) complex of claim 12, wherein the $RuCl_3$ in ethanol is added stepwise.

14. The method of making nano-sized [4{3,4-bis-[(5-bromo-2-hydroxy-benzylidene)-amino]-phenyl}-phenyl-methanone] Ru(III) complex of claim 12, wherein sonicating the reaction mixture a first time lasts for about 30 minutes.

15. The method of making nano-sized [4{3,4-bis-[(5-bromo-2-hydroxy-benzylidene)-amino]-phenyl}-phenyl-methanone] Ru(III) complex of claim 12, wherein sonicating the reaction mixture a second time lasts for about 30 minutes.

16. The method of making nano-sized [4{3,4-bis-[(5-bromo-2-hydroxy-benzylidene)-amino]-phenyl}-phenyl-methanone] Ru(III) complex of claim 12, wherein the $RuCl_3$ and the 4{3,4-Bis-[(5-bromo-2-hydroxy-benzylidene)-amino]-phenyl}-phenyl-methanone azomethine ligand are added in an about 2:1 molar ratio.

17. The method of making the nano-sized [4{3,4-bis-[(5-bromo-2-hydroxy-benzylidene)-amino]-phenyl}-phenyl-methanone] Ru(III) complex of claim 12, wherein the $RuCl_3$, the 4{3,4-Bis-[(5-bromo-2-hydroxy-benzylidene)-amino]-phenyl}-phenyl-methanone azomethine ligand, and the secondary ligand phenanthroline are added in an about 2:1:1 molar ratio.

18. The method of making nano-sized [4{3,4-bis-[(5-bromo-2-hydroxy-benzylidene)-amino]-phenyl}-phenyl-methanone] Ru(III) complex of claim 12, wherein the nano-sized [4{3,4-bis-[(5-bromo-2-hydroxy-benzylidene)-amino]-phenyl}-phenyl-methanone] Ru(III) complex is obtained as a dark brown crystalline powder.

\* \* \* \* \*